(12) United States Patent
Blocher et al.

(10) Patent No.: US 9,554,858 B2
(45) Date of Patent: Jan. 31, 2017

(54) TOOL FOR A MEDICAL INSTRUMENT (71) Applicant: Karl Storz GmbH & Co. KG, Tuttlingen (DE)

(72) Inventors: Martin Blocher, Stockach-Espasingen (DE); Robin Merz, Furtwangen (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 147 days.

(21) Appl. No.: 13/865,628

(22) Filed: Apr. 18, 2013

(65) Prior Publication Data

US 2013/0302084 A1 Nov. 14, 2013

(30) Foreign Application Priority Data

Apr. 18, 2012 (DE) .......................... 10 2012 007 647

(51) Int. Cl.
*A61B 17/32* (2006.01)
*A61B 19/00* (2006.01)
*F16C 11/04* (2006.01)
*A61B 17/00* (2006.01)
*A61B 17/29* (2006.01)
*A61B 17/295* (2006.01)
*A61B 17/3211* (2006.01)
*A61B 18/14* (2006.01)
*A61B 18/00* (2006.01)

(52) U.S. Cl.
CPC ......... *A61B 19/22* (2013.01); *A61B 17/00234* (2013.01); *A61B 17/29* (2013.01); *A61B 17/295* (2013.01); *A61B 18/1445* (2013.01); *F16C 11/04* (2013.01); *A61B 17/3211* (2013.01); *A61B 2017/2902* (2013.01); *A61B 2017/2933* (2013.01); *A61B 2017/2934* (2013.01); *A61B 2017/2939* (2013.01); *A61B 2017/2947* (2013.01); *A61B 2018/00607* (2013.01); *A61B 2018/1455* (2013.01); *Y10T 403/32951* (2015.01)

(58) Field of Classification Search
CPC ..................... A61B 17/295; A61B 2017/2934; A61B 17/29; A61B 17/3211; A61B 17/00234; A61B 2017/2933; A61B 2017/2939
USPC ......................................................... 606/208
See application file for complete search history.

(56) References Cited

U.S. PATENT DOCUMENTS

| | | | |
|---|---|---|---|
| 5,673,841 A | 10/1997 | Schulze et al. | |
| 5,683,359 A | 11/1997 | Farkas et al. | |
| 5,697,949 A * | 12/1997 | Giurtino et al. | ............... 606/205 |
| 7,105,000 B2 | 9/2006 | McBrayer | |
| 7,857,827 B2 | 12/2010 | Measamer | |
| 7,976,552 B2 | 7/2011 | Suzuki | |

(Continued)

FOREIGN PATENT DOCUMENTS

DE 202007009315 U1 8/2007
EP 1468653 A2 10/2004

(Continued)

*Primary Examiner* — Robert Lynch
(74) *Attorney, Agent, or Firm* — Whitmyer IP Group LLC (57) ABSTRACT

A tool for a distal end or on a distal end of a shaft of a medical instrument includes a basic body, a mouth part which is pivotable about a pivot axis in relation to the basic body, and a bearing which defines the pivot axis, wherein the bearing includes two axle journals which are spaced apart from one another, each with a radial surface which is rotationally symmetrical with respect to the pivot axis.

10 Claims, 4 Drawing Sheets

(56) References Cited

U.S. PATENT DOCUMENTS

2005/0033312 A1* 2/2005 Suzuki .......................... 606/110
2009/0018573 A1* 1/2009 Teichtmann ....... A61B 17/1608
                                                          606/207

FOREIGN PATENT DOCUMENTS

| EP | 1927320 | A2 | 6/2008 |
| EP | 2077773 | B1 | 12/2011 |
| WO | 2008040486 | A2 | 4/2008 |

\* cited by examiner

TOOL FOR A MEDICAL INSTRUMENT

FIELD OF THE INVENTION

The present invention relates to a tool for a distal end or on a distal end of a shaft of a medical instrument and to a medical instrument having such a tool.

BACKGROUND OF THE INVENTION

Medical devices and medical personnel prefer medical instruments which can be used as variously as possible. The more variously the individual medical instrument can be used, the smaller the variety of instruments to be held in readiness. Variously usable medical instruments, consequently, can reduce the investment costs necessary in a medical setup even where unit costs are high. A small variety and a smaller number of medical instruments to be kept in readiness can also reduce costs for storage and logistics.

In the case of micro-invasive medical instruments or medical instruments for micro-invasive interventions, there is also the fact that during an intervention the less often instruments have to be changed, the more variously the individual instrument can be used.

SUMMARY OF THE INVENTION

An object of the present invention is to create an improved tool for a distal end or on a distal end of a medical instrument and an improved medical instrument. An object, in particular, is, in the case of a tool with a pivotable mouth part, to make possible an operating channel in which a scalpel or another acting element is able to be arranged and moved.

This object is achieved by the objects of the independent claims.

Further developments are provided in the dependent claims.

A tool for a distal end or on a distal end of a shaft of a medical instrument includes a basic body, a mouth part which is pivotable about a pivot axis in relation to the basic body, and a bearing which defines the pivot axis, wherein the bearing includes two axle journals which are spaced apart from one another, each with a radial surface which is rotationally symmetrical with respect to the pivot axis.

The tool is realized for (in particular detachable) mechanical coupling with the distal end of a shaft or is mechanically connected (in particular so as to be detachable without damage) to the distal end of a shaft. In this case, the shaft is a component part of a medical instrument or is provided for forming a medical instrument.

At the proximal end or in a proximal region, the basic body has a coupling for the detachable mechanical coupling with a distal end of a shaft. As an alternative to this, the basic body is mechanically connected to the distal end of a shaft in a permanent manner and so as to be detachable without damage. The tool can have a further mouth part which is not movable in relation to the basic body. Said further mouth part is connected in particular to the basic body in a rigid manner or is realized integrally with said basic body. As an alternative to this or in addition to it, the tool can have one or several further movable, in particular pivotable, mouth parts.

The bearing can include more than two axle journals which are spaced apart from one another, each having a radial surface which is rotationally symmetrical with respect to the pivot axis of the mouth part. Each individual axle journal is connected in a rigid manner either to the pivotable mouth part or to the basic body.

As described below and as is shown in detail by way of the exemplary embodiments, the two (or more) axle journals, which are spaced apart from one another, create new structural degrees of freedom.

A tool, as is described here, additionally includes, in particular, an operating channel in which a scalpel or another acting element can be displaced between a proximal and a distal position.

The scalpel is provided and realized, in particular, for cutting through tissue which is grasped by means of the tool. For example, the tool is realized for the monopolar or bipolar electro-cauterization of tissue grasped by means of the tool. A vessel or other tissue can be grasped, squeezed, scelerosed electro-surgically or HF-surgically by means of the tool and then cut through by means of the scalpel. The ability to carry out all of said procedure steps using one single tool can clearly reduce the time taken for a micro-surgical intervention. Instead of for a scalpel, the operating channel can be usable for other working elements which can be inserted with the tool in an open and/or a closed position.

In the case of a tool with an operating channel, as is described here, the operating channel is arranged, in particular, between the axle journals.

The operating channel extends, in particular, from a handling device along a shaft as far as up to the tool and to the active region of the pivotable mouth part. An arrangement of the operating channel between the axle journals means that the operating channel leads through between the axle journals or at least part of the lumen of the operating channel lies between the axle journals.

In the case of an almost arbitrary arrangement of the pivot axis of the pivotable mouth part, the bearing with two (or more) axle journals, which are spaced apart from one another, makes possible a large cross section or a large lumen of the operating channel, at least in the direction at right angles with respect to the longitudinal axis of the tool and at right angles with respect to the pivot axis. Comparable cross sections of the operating channel are possible in the case of a bearing with a continuous shaft at most where the shaft is arranged at a large spacing from the center of the cross section and there is a small spacing between the shaft and the outer edge of the cross section of the tool. However, said arrangement of the shaft is only possible with a circular cross section of the tool if the shaft is short, which results in other structural disadvantages.

In the case of a tool, as is described here, the basic body of the tool includes, in particular, two parallel walls, between which a portion of the operating channel is arranged, wherein each of the two parallel walls has a recess in which one of the two axle journals engages.

The two parallel walls are realized, in particular, as webs on a base plate.

The two (or more) parallel walls are arranged, in particular, parallel with respect to the longitudinal axis of the tool or of a shaft which is connected to the tool or is to be connected to the tool and at right angles with respect to the pivot axis of the pivotable mouth part. The two parallel walls define, in particular, the operating channel on two opposite sides such that the operating channel is defined at least in portions by the two opposite walls. Each recess is formed, in particular, by a blind hole in one of the two parallel walls. As an alternative to this, the two recesses are formed by one single through-bore which penetrates the two parallel walls.

In the case of a tool, as is described here, the bearing includes additionally, in particular, recesses which correspond to the axle journals, wherein the axial pins engage in the recesses from the outside.

As already mentioned for the embodiment with two parallel walls, in other cases the recesses which correspond to the axle journals can also be formed by one single through-bore, the axle journals engaging in the two opposite ends of the through-bore. The term engage from the outside refers to an engagement from two opposite directions where the axle journals project toward one another.

In the case of a tool, as is described here, the bearing additionally, in particular, includes recesses which correspond to the axle journals, wherein the axial pins engage in the recesses from the inside.

The phrase the axle journals engage in the recesses from the inside refers to the axle journals projecting in two opposite directions facing away from one another.

In the case of a tool, as is described here, the mouth part includes, in particular, two axle journal components each with one of the axle journals.

Each axle journal component is produced, in particular, in one piece. At the proximal end thereof, each axle journal component includes, in particular, the associated axle journal and an arm or bar which extends substantially at right angles with respect to the pivot axis of the pivotable mouth part. If the axle journal components are component parts of the pivotable mouth part, the arms or bars are connected, in particular, to the pivotable mouth part, are arranged in said mouth part or form the pivotable mouth part.

As an alternative to this, the arms or bars are connected in a rigid manner to the basic body of the tool, and the axle journals engage in recesses which are provided on the pivotable mouth part.

In the case of a tool with two axle journal components, as is described here, the axle journal components have been connected together in a rigid manner once the axle journals have been inserted into the corresponding recesses.

In particular, once the axle journals have been inserted in the corresponding recesses, the already mentioned arms or bars have been joined together directly or indirectly in order to form, for example, the pivotable mouth part.

In the case of a tool with axle journal components which have been connected together in a rigid manner once the axle journals have been inserted in the corresponding recesses, the axle journal components are connected together in a rigid manner, in particular, by means of a basic body of the pivotable mouth part.

In particular, the mentioned arms or bars of the axle journal components are inserted into bores or grooves in the basic body of the pivotable mouth part and are joined.

A tool, as is described here, includes additionally, in particular, a transferring device for transferring a force to the tool, wherein the transferring device and the pivotable mouth part have curved sliding faces which abut against one another and are realized for the purpose of coupling a translation movement of the transferring device with a pivoting movement of the pivotable mouth part, wherein a center of curvature of the curved sliding faces lies outside the tool.

The transferring device is slidable, in particular, lengthwise of a shaft which is couplable to the tool or is connected in a permanent manner. The transferring device can be coupled in such a manner with the mouth part by means of the curved sliding faces, which abut against one another, that a movement of the transferring device in the proximal direction brings about a closing pivoting movement of the mouth part or, as an alternative to this, in a reverse manner brings about an opening movement of the mouth part. The transferring device, in this case, is guided, in particular, inside the tool or inside a shaft which is couplable with the tool or is permanently connected to the tool, such that it is slidable along a substantially straight or slightly curved path.

The sliding faces of the transferring device and of the pivotable mouth part, in each case abutting against one another in pairs, have, in particular, a common center of curvature or are rotationally symmetrical with respect to an axis. Said substantially arcuate development of the sliding faces enables flat contact which can be suitable for transferring large forces.

As an alternative to this, the sliding faces can have several centers of curvature or a varying curvature or a development which is not rotationally symmetrical with respect to an axis. With said resultant non-arcuate development of the sliding faces, a varying transformation ratio can be realized between the movement of the transferring device and the pivoting movement of the pivotable mouth part.

The arrangement of the center of curvature of the curved sliding faces makes possible a large transformation ratio where a translation movement of the transferring device along a relatively long path is necessary for a predetermined pivoting movement of the pivotable mouth part.

In the case of a tool with curved sliding faces, abutting against one another, on the transferring device and the pivotable mouth part, as is described here, in particular the curved sliding faces on the mouth part are parallel faces on a curved groove and the curved sliding faces on the transferring device are parallel faces on a curved web. As an alternative to this, the curved sliding faces on the mouth part can be parallel faces on a curved web and the curved sliding faces on the transferring device can be parallel faces on a curved groove. As an alternative to this, the curved sliding faces can be non-parallel.

In the case of a tool, as is described here, the pivot axis about which the pivotably mounted mouth part is pivotable lies in particular inside the tool.

An arrangement of the pivot axis inside the tool refers to the fact that the pivot axis intersects or penetrates the volume assumed by the tool. In other words, a portion of the pivot axis lies inside the contour of the tool.

In the case of a tool, as is described here, a groove is provided inside a circular cylindrical region of space, in particular, on at least one of the two axle journals, wherein the radial surface of the axle journals lies on a radial surface of the circular cylindrical region of space.

Side walls of the groove lying opposite one another form, in particular, the mentioned curved sliding faces on the pivotable mouth part. In particular, a web on the mentioned transferring device engages in the groove.

A medical instrument includes a tool, as is described here.

BRIEF DESCRIPTION OF THE DRAWINGS

Embodiments are explained below by way of the accompanying figures, in which, in detail.

DETAILED DESCRIPTION OF THE INVENTION

Figure 1:
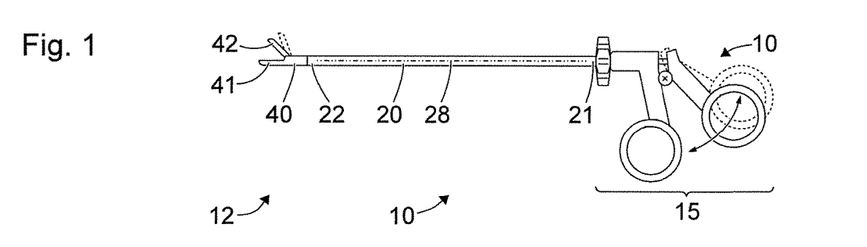
FIG. 1 shows a schematic representation of a medical instrument.

FIG. 1 shows a schematic representation of a medical instrument 10 which is realized, in particular, for microinvasive surgical interventions. At the proximal end 11 thereof, the medical instrument 10 includes a handling device 15 and at the distal end 12 thereof it includes a tool 40. A straight or curved, rigid or flexible shaft 20 connects the handling device 15 and the tool 40. The proximal end 21 of the shaft 20 is connected to the handling device 15, the distal end 22 of the shaft 20 is connected to the tool 40.

Two parts of the handling device 15 are movable in relation to one another. One of the two parts is connected in a rigid manner to the tool 40 by means of the shaft 20, the other part of the handling device 15 is coupled with a pivotable mouth part 42 of the tool 40 by means of a transferring device (in particular a transferring rod) which is arranged in the shaft 20. A manually activated relative movement of the two parts of the handling device 15 results in a corresponding relative movement of the pivotable mouth part 42 in relation to a fixed mouth part 41 of the tool 40.

Figure 2:
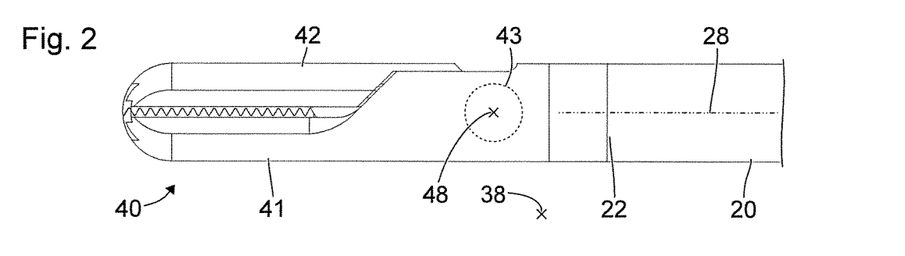
FIG. 2 shows a schematic representation of a tool of the medical instrument from FIG. 1.

FIG. 2 showed an enlarged schematic representation of a tool 40 which is similar to the tool shown above by way of FIG. 1 and is usable on medical instruments which are similar to that shown above by way of FIG. 1.

The tool 40 is coupled mechanically with the distal end 22 of a shaft 20 so as to be detachable or is permanently connected thereto. The tool 40 includes a fixed mouth part 41 and a pivotable mouth part 42. The fixed mouth part 41 is arranged in a rigid manner in relation to the shaft 20. The pivotable mouth part 42 is pivotable in relation to the fixed mouth part 41 about a pivot axis 48 at right angles with respect to the drawing plane of FIG. 2. The pivot axis 48 is defined by a bearing 43 which is arranged in the interior of the tool 40 and is indicated by the broken line in FIG. 2. A center of curvature 38 is described in more detail below with reference to FIGS. 12 and 13.

Figure 3:
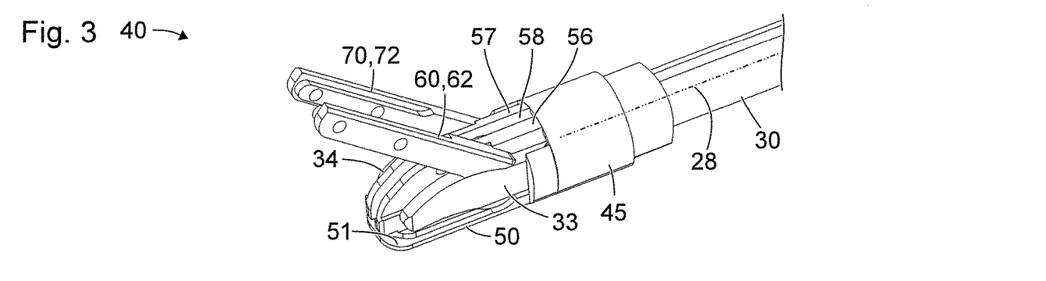
FIG. 3 shows a schematic axonometric representation of parts of the tool from FIG. 2.
Figure 4:
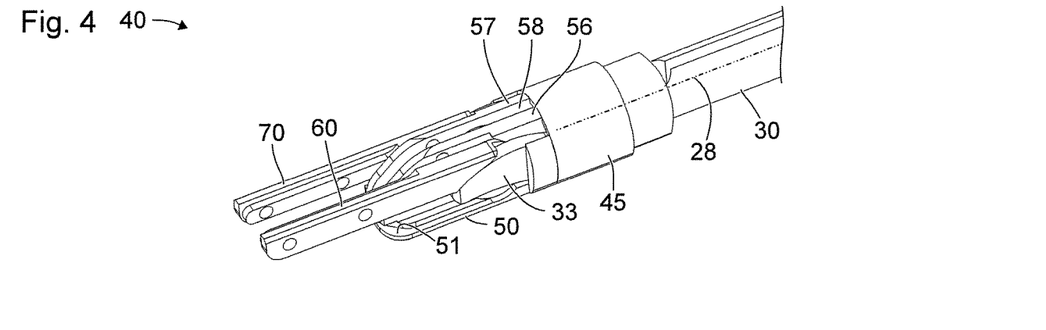
FIG. 4 shows a further schematic axonometric representation of parts of the tool from FIGS. 2 and 3.

FIGS. 3 and 4 show schematic axonometric representations of parts of the tool 40 from FIG. 2. The tool 40 includes a basic body 50 with a base plate 51 with a step-shaped profiled edge. The base plate 51 extends substantially parallel with respect to the longitudinal axis of a shaft to be connected to the tool 40 and at right angles with respect to the drawing planes of FIGS. 1 and 2. A first longitudinal web 56 and a second longitudinal web 57 are arranged at right angles with respect to the base plate 51. The two longitudinal webs 56, 57 extend parallel with respect to the longitudinal axis of a shaft to be connected to the tool 40 and parallel to the drawing planes of FIGS. 1 and 2. Between the longitudinal webs 56, 57 is provided a narrow operating channel 58, which extends, as the longitudinal webs 56, 57, parallel with respect to the longitudinal axis 28 of a shaft to be connected to the tool 40 as far as up to the distal end of the basic body 50. The two longitudinal webs 56, 57 are connected by a connecting pin 59 close to the edges thereof which are at a spacing from the base plate 51. The connecting pin 59 extends at right angles with respect to the longitudinal axis 28 of a shaft to be connected to the tool 40 and at right angles with respect to the drawing planes of FIGS. 1 and 2.

A first axle journal component 60 and a second axle journal component 70 are realized in a mirror symmetrical manner with respect to one another and are connected to the basic body 50 so as to be pivotable. Features of the bearing arrangement of the axle journal components 60, 70 on the basic body 50 are described in more detail below with reference to FIGS. 5 to 7. The axle journal components 60, 70, in particular a bar 62 of the first axle journal component 60 and a bar 72 of the second axle journal component 70, are component parts of the pivotable mouth parts 42 shown in FIGS. 1 and 2.

A transferring device 30 extends in the shaft 20 (cf. FIG. 1) from the handling device 15 as far as up to the tool 40. On the distal end, the transferring device 30 includes two parallel bars 33, 34 which are realized in a mirror-symmetrical manner with respect to one another. Only the first bar 33 can be seen clearly in FIGS. 3 and 4, the second bar 34 is extensively covered. The bars 33, 34 on the distal end of the transferring device 30 are arranged on both sides of the longitudinal webs 56, 57 of the basic body 50.

A sleeve 45 is arranged on the proximal end of the basic body 50. The sleeve 45, in the example shown, has cross section which varies in a step-shaped manner. The sleeve 45 surrounds the transferring device 30 or the bars 33, 34 thereof in a ring-shaped manner. A coupling for the detachable mechanical coupling of the tool 40 with a distal end 22 of a shaft 20 (cf. FIGS. 1 and 2) is arranged on the proximal edge of the sleeve 45.

Each bar 33, 34 has a curved web which engages in a curved groove on one of the axle journal components 60, 70. Said webs on the bars 33, 34 and the grooves on the axle journal components 60, 70 cannot be seen in FIGS. 3 and 4, but will be described below with reference to FIGS. 5 to 7, 12 and 13. The engagement of the webs on the bars 33, 34 in the grooves on the axle journal components 60, 70 couples a translation movement of the transferring device 30 and a pivoting movement of the axle journal components 60, 70 together.

FIG. 3 shows the transferring device 30 in a distal position and the axle journal components 60, 70 or the bars 62, 72 thereof in open positions which correspond to the distal position of the transferring device 30. FIG. 4 shows the transferring device 30 in a proximal position and the axle journal components 60, 70 or the bars thereof 62, 72 in closed positions which correspond to the proximal position of the transferring device 30.

Figure 5:
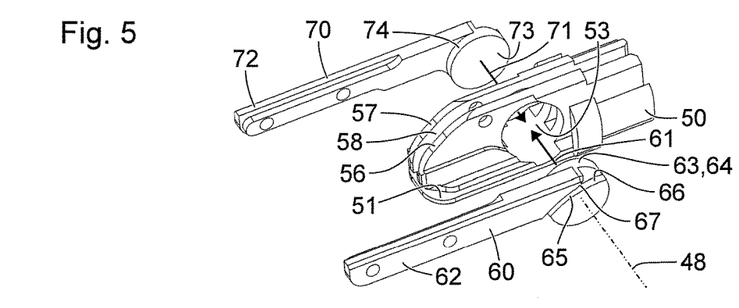
FIG. 5 shows a further schematic axonometric representation of parts of the tool from FIGS. 2 to 4.

FIG. 5 shows a schematic axonometric representation of the basic body 50 and of the axle journal components 60, 70 prior to insertion of the axle journal components 60, 70 into the basic body 50. The basic body 50 has a recess 53 in the form of a through-bore at right angles with respect to the longitudinal axis 28 (cf. FIGS. 1 to 4) and parallel with respect to the pivot axis 48 of the pivotable mouth part 42 (cf. FIG. 2). The through-bore 53 penetrates both longitudinal webs 56, 57 of the basic body 50. The first axle journal component 60 includes an axle journal 63 with a narrow ring-shaped radial surface 64. The second axle journal component 70 includes an axle journal 73 with a narrow ring-shaped radial surface 74.

The axle journals 63, 73 can be inserted into the recess 53 on the basic body 50 by means of insertion movements 61, 71, indicated by means of arrows, parallel to the pivot axis 48. The recess 53 has a circular cross section which is tuned in such a manner to the radial surfaces 64, 74 of the axle journals 63, 73 that the axial pins 63, 73, once they have been inserted 61, 71 into the recess 53, are guided on the basic body low in play and friction. The recess 53 in the basic body 50 and the axle journals 63, 73 engaging in the recess 53 form the joint or bearing 43 which has already been indicated in FIG. 2 and defines the pivot axis 48 of the pivotable mouth part 42. The widths of the ring-shaped radial surfaces 64, 74 of the axle journals 63, 73 correspond substantially to the wall thicknesses of the longitudinal webs 56, 57 on the basic body 50.

Figure 6:
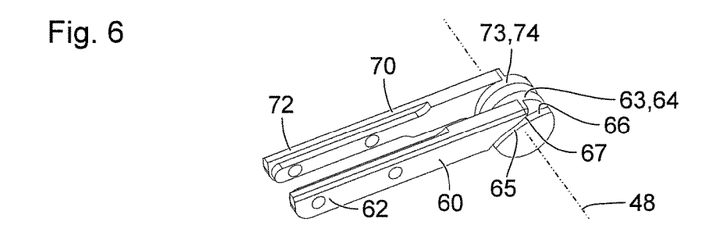
FIG. 6 shows a further schematic axonometric representation of parts of the tool from FIGS. 2 to 5.

FIG. 6 shows a further schematic axonometric representation of the axle journal components 60, 70 from FIGS. 3 to 5. The axle journal components 60, 70 are shown in the relative position and spaced apart as they are when the axle journals 63, 73 of the axle journal components 60, 70 are inserted fully into the recess 53 on the basic body 50 (cf. FIG. 5). The basic body 50, however, is not shown in FIG. 6. The axle journals 63, 73 or the circular end faces thereof are at a spacing which corresponds substantially to the width of the operating channel 58 between the longitudinal webs 56, 57 on the basic body 50 (cf. FIGS. 3 to 5). In other words, the axle journals 63, 73 do not engage in the operating channel 58 nor restrict the lumen or cross section thereof.

Figure 7:
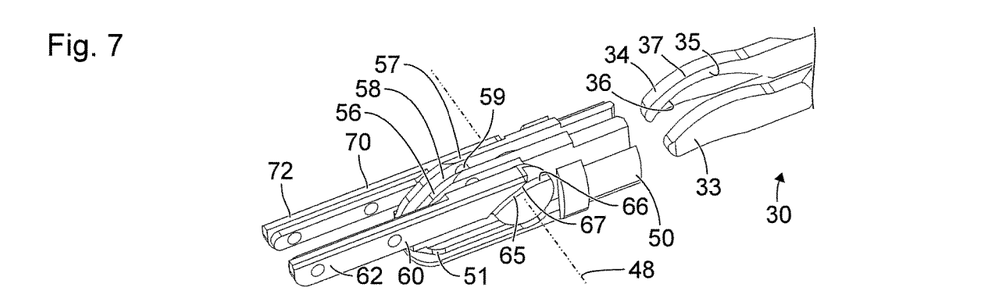
FIG. 7 shows a further schematic axonometric representation of parts of the tool from FIGS. 2 to 6.

FIG. 7 shows a schematic axonometric representation of the basic body 50 and of the axle journal components 60, 70. The axle journals 63, 73 (cf. FIGS. 5 and 6) of the axle journal components 60, 70 are inserted into the recess 53 (cf. FIG. 5) in the basic body 50. In addition, the distal end of the transferring device 30 with the bars 33, 34 is shown. The bars 33, 34, however, have not yet been inserted into the basic body 50 and coupled with the axle journal components 60, 70.

A curved groove 65 can be seen in the first axle journal component 60 in FIGS. 5 to 7. The curved groove 65 has two substantially parallel curved sliding faces 66, 67 which are, however, variously wide. The groove 65 essentially extends totally inside the region of the axle journal 63, more precisely inside a circular cylindrical region of space, the radial surface of which corresponds in portions to the radial surfaces 64, 74 of the axle journals 63, 73 of the axle journal components 60, 70 (cf. FIGS. 5 and 6). The second axle journal component 70 is realized in a mirror symmetrical manner to the first axle journal component 60 and has, in particular, a curved groove, which corresponds mirror symmetrically to the groove 65 on the first axle journal component 60 and is not able to be seen in FIGS. 5 to 7.

A curved web 35 with a first sliding face 36 and a second sliding face 37 can be seen on the second bar 34 on the distal end of the transferring device 30. The first bar 33 has a web which is curved in a mirror-symmetrical manner to the curved web 35 on the second bar 34. The widths and the curvatures of the curved grooves 65 on the axle journal components 60, 70 and the widths and the curvatures of the webs 35 on the bars 33, 34 of the transferring device 30 correspond to one another such that the webs 35 on the bars 33, 34 are guided low in play and friction in the grooves 65 on the axle journal components 60, 70 when the distal end of the transferring device 30 is inserted into the basic body 50 and the axle journal components 60, 70.

After inserting the axle journals 63, 73 into the recess 53 in the basic body 50 and coupling the bars 33, 34 with the axle journal components 60, 70 by inserting the curved web 35 into the curved groove 65, the bars 62, 72 of the axle journal components 60, 70 are connected together by a basic body (not shown in FIGS. 3 to 7) of the pivotable mouth part 42 (cf. FIGS. 1 and 2). The basic body of the pivotable mouth part 42 has, in particular, bores or grooves into which the bars 62, 72 of the axle journal components 60, 70 are inserted. The mentioned basic body of the pivotable mouth part 42 holds the axle journal components 60, 70 in their relative position shown in FIGS. 3, 4, 6 and 7 and consequently holds the axle journals 63, 73 in the recess 53 in the basic body 50.

Figure 8:
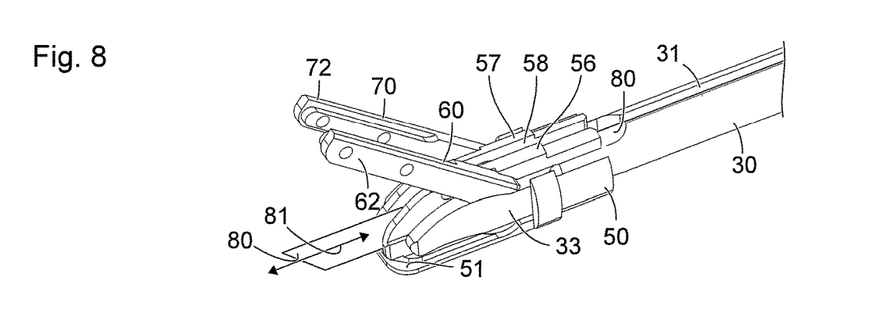
FIG. 8 shows a further schematic axonometric representation of parts of the tool from FIGS. 2 to 7.
Figure 9:
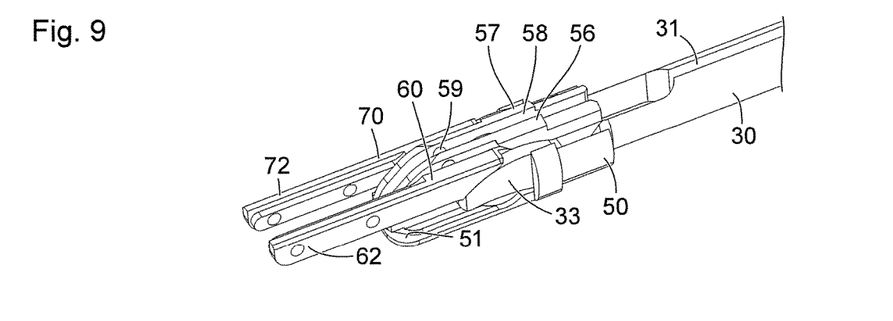
FIG. 9 shows a further schematic axonometric representation of parts of the tool from FIGS. 2 to 8.

FIGS. 8 and 9 show schematic axonometric representations of the basic body 50, the axle journal components 60, 70 and the transferring device 30. The representations in FIGS. 8 and 9, with regard to the positions of the transferring device 30 and of the axle journal components 60, 70, correspond to the representations in FIG. 3 or 4. Contrary to the representations in FIGS. 3 and 4, the sleeve 45 on the proximal end of the basic body 50 is not shown in FIGS. 8 and 9. As a result, the first bar 33 is visible to a greater extent. It can be seen in FIGS. 5 to 9 that the basic body 50, parallel to the operating channel 58 and on the outside abutting against the two longitudinal webs 56, 57, has two grooves in which the bars 33, 34 are guided (cf. FIG. 7).

FIG. 8 also shows a scalpel 80 which is arranged in the operating channel 58 of the basic body 50 so as to be slidable in the direction 81 parallel to the longitudinal axis 28 (cf. FIGS. 1 to 4). Proximally of the basic body 50, the scalpel 80 lies in a groove 31 in the transferring device 30 which continues the operating channel 58 in the proximal direction. In particular, the scalpel 80 extends as far as up to the handling device 15 (cf. FIG. 1) in order to make a movement of the scalpel 80 possible from the handling device 15. Corresponding devices on the handling device 15 are not shown in FIG. 1.

Figure 10:
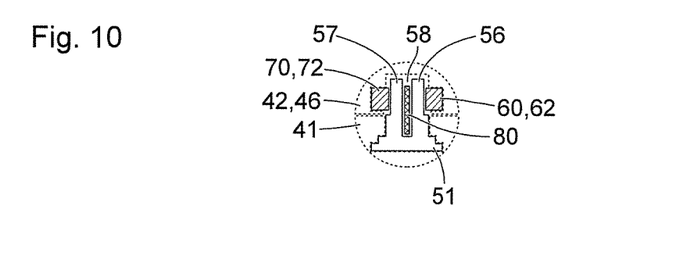
FIG. 10 shows a schematic representation of a section through the tool from FIGS. 2 to 9.
Figure 11:
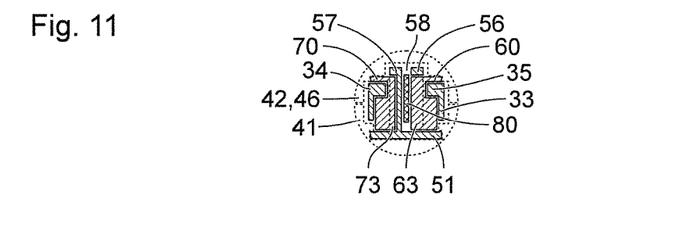
FIG. 11 shows a schematic representation of a further section through the tool from FIGS. 2 to 10.

FIGS. 10 and 11 show schematic representations of cross sections through the basic body 50, the axle journal components 60, 70 and the scalpel 80. FIG. 11 also shows cross sections of the bars 33, 34. The contours of the mouth parts 41, 42 are indicated by the dotted lines. Both FIGS. 10 and 11 show the pivotable mouth part 42 with the axle journal components 60, 70 in the closed position which is also shown in FIGS. 2, 4, 7 and 9.

The cutting planes of FIGS. 10 and 11 are at right angles with respect to the longitudinal axis 28 (cf. FIGS. 1 to 4) and to the drawing planes of FIGS. 1 and 2. The cutting plane of FIG. 10 is distally of the connecting pin 59 between the longitudinal webs 56, 57 of the basic body 50 (cf. FIGS. 4 and 9). The cutting plane of FIG. 11 includes the pivot axis 48 of the pivotable mouth part 42 (cf. FIGS. 2 and 5 to 7).

The design of the basic body 50 with the base plate 51 arranged horizontally in FIGS. 10 and 11 and the longitudinal webs 56, 57 arranged vertically in FIGS. 10 and 11 can be seen in each case in FIGS. 10 and 11. In addition, the operating channel 58 between the longitudinal webs 56, 57 and the scalpel 80 in the operating channel 58 can also be seen. The cutting plane of FIG. 10 intersects the two bars 62, 72 of the axle journal components 60, 70. The cutting plane of FIG. 11 intersects the axle journals 63, 73 of the axle journal components 60, 70 and the bars 33, 34 of the transferring device 30 (cf. FIGS. 3, 4, 8 and 9). It can be seen in the cross section shown in FIG. 11 how the webs 35 on the bars 33, 34 engage in the corresponding grooves on the axle journal components 60, 70.

In addition, it can be seen how the axle journals 63, 73 engage in the longitudinal webs 56, 57 of the basic body 50. In this case, FIG. 11 shows two different variants of the axle journals 63, 73. The axle journal 63 of the first axle journal component 60 engages in a corresponding recess, which is realized as a through-bore, in the first longitudinal web 56 and reaches as far as up to the operating channel 58. The axle journal 73 on the second axle journal component 70 engages in a recess, which is realized as a blind hole, on the second longitudinal web 57 of the basic body 50. The axle journal 73 of the second axle journal component 70 is consequently separated from the operating channel 58 by a thin region of the second longitudinal web 57. Deviating from the representation in FIG. 11, a tool has, in particular, two mirror-symmetrical axle journal components 60, 70 and two mirror-symmetrical longitudinal webs 56, 57. The engagement of the two axle journals in the longitudinal webs 56, 57 corresponds consequently, in particular, either to the first axle journal 63 shown in FIG. 11 in the first longitudinal web 56 or to the second axle journal 73 shown in FIG. 11 in the second longitudinal web 57.

In addition, the basic body 46, already mentioned in the description of FIGS. 5 to 7, can be seen in FIGS. 10 and 11, said basic body holding the axle journal components 60, 70 in their relative position shown in FIGS. 3, 4, 6 and 7 and consequently holding the axle journals 63, 73 in the recess 53 in the basic body 50. To this end, the basic body 46 has grooves, which can be seen, in particular, in FIG. 10 and in which the bars 62, 72 of the axle journal components 60, 70 are held in a positive locking manner.

Figure 12:
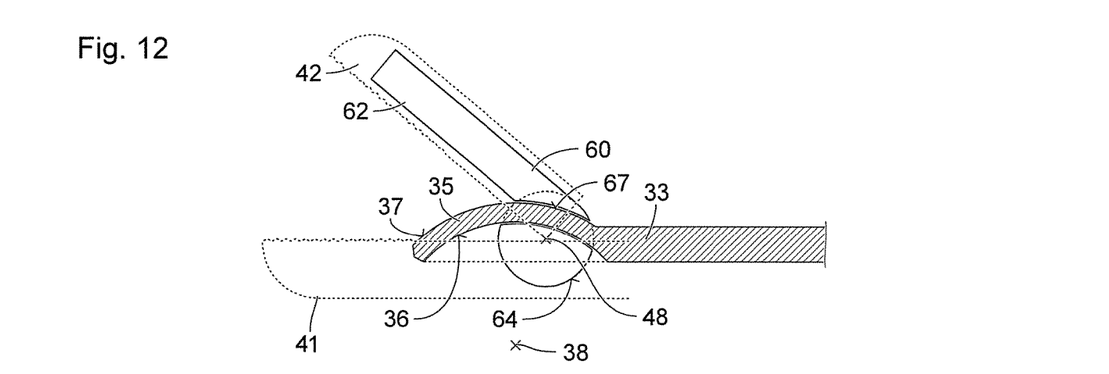
FIG. 12 shows a further schematic representation of parts of the tool from FIGS. 2 to 11.
Figure 13:
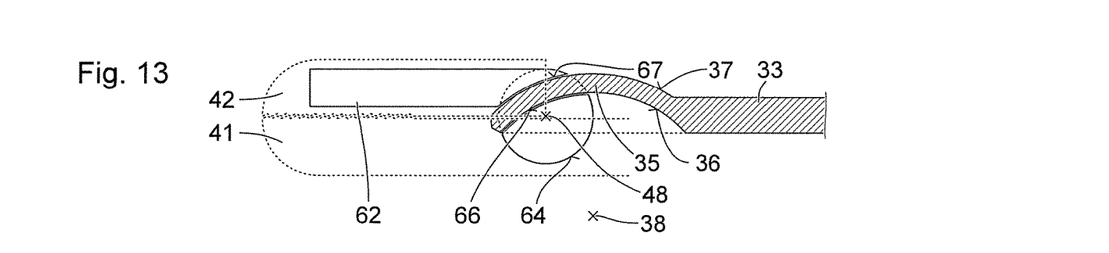
FIG. 13 shows a further schematic representation of parts of the tool from FIGS. 2 to 12.

FIGS. 12 and 13 show schematic representations of a section through the first bar 33 and the first axle journal component 60 (cf. FIGS. 3 to 11). The cutting planes of FIGS. 12 and 13 are parallel to the longitudinal axis 28 (cf. FIGS. 1 to 4), to the drawing planes of FIGS. 1 and 2 and at right angles to the pivot axis 48 of the pivotable mouth part 42 (cf. FIGS. 2 and 5 to 7) as well as to the cutting planes of FIGS. 10 and 11. The cutting planes of FIGS. 12 and 13 are arranged such that they intersect the groove 65 on the first axle journal component 60 and the web 35 on the first bar 33. The contours of the fixed mouth part 41 and of the pivotable mouth part 42 are indicated by the dotted lines.

FIG. 12 shows the bar 33 in the distal position and the pivotable mouth part 42 with the axle journal component 60 in the open position, these are also shown in FIGS. 3 and 8. FIG. 13 shows the bar 33 in the proximal position and the pivotable mouth part 42 with the axle journal component 60 in the closed position, these are also shown in FIGS. 4 to 7 and 9 to 11. In addition, FIGS. 12 and 13 show the center of curvature 38 of the curved web 35 on the bar 33 (and consequently of the sliding faces 36, 37 on the curved web 35) and of the curved groove 65 (cf. FIGS. 5 to 7) on the axle journal component 60 (and consequently of the sliding faces 66, 67 of the curved groove). The center of curvature 38 lies outside the tool 40 or outside the contours thereof, which are indicated in FIGS. 12 and 13 by the dotted lines.

List of references

| | |
|---|---|
| 10 | Medical instrument |
| 11 | Proximal end of the medical instrument 10 |
| 12 | Distal end of the medical instrument 10 |
| 15 | Handling device |
| 20 | Shaft of the medical instrument 10 |

-continued

List of references

| | |
|---|---|
| 21 | Proximal end of the shaft 20 |
| 22 | Distal end of the shaft 20 |
| 28 | Longitudinal axis of the shaft 20 |
| 30 | Transferring device |
| 31 | Longitudinal groove in the transferring device 30 |
| 32 | Distal end of the transferring device 30 |
| 33 | First bar on the distal end of the transferring device 30 |
| 34 | Second bar on the distal end of the transferring device 30 |
| 35 | Curved web on a bar 33, 34 |
| 36 | First sliding face on the web 25 |
| 37 | Second sliding face on the web 35 |
| 38 | Center of curvature of the web 35 |
| 40 | Tool |
| 41 | Fixed mouth part of the tool 40 |
| 42 | Pivotable mouth part of the tool 40 |
| 43 | Bearing |
| 45 | Sleeve |
| 46 | Basic body of the pivotable mouth part 42 |
| 48 | Pivot axis of the pivotably mounted mouth part 40 |
| 50 | Basic body of the tool 40 |
| 51 | Base plate of the basic body 50 |
| 53 | Recess on the basic body 50 |
| 56 | First longitudinal web on the basic body 50 |
| 57 | Second longitudinal web on the basic body 50 |
| 58 | Operating channel between the longitudinal webs 56, 57 of the basic body 50 |
| 59 | Connecting pin |
| 60 | First axle journal component of the pivotably mounted mouth part 42 |
| 61 | Insertion movement |
| 62 | Bar of the first axle journal component 60 |
| 63 | Axle journal on the first axle journal component 60 |
| 64 | Radial surface of the axle journal 63 |
| 65 | Groove on the first axle journal component 60 |
| 66 | First sliding face on the groove 65 |
| 67 | Second sliding face on the groove 65 |
| 70 | Second axle journal component of the pivotably mounted mouth part 40 |
| 71 | Insertion movement |
| 72 | Bar of the second axle journal component 70 |
| 73 | Axle journal on the second axle journal component 70 |
| 74 | Radial surface of the axial pin 73 |
| 80 | Scalpel |
| 81 | Direction of movement of the scalpel 80 |

The invention claimed is:

1. A tool for a distal end or on a distal end of a shaft of a medical instrument, said tool comprising:
a basic body;
a mouth part which is pivotable about a pivot axis in relation to the basic body;
a bearing arranged entirely in an interior of the tool which defines the pivot axis, the bearing including two axle journals, the two axle journals being spaced apart from one another along the pivot axis, each axle journal having a radial surface which is rotationally symmetrical with respect to the pivot axis;
the mouth part includes two axle journal components each corresponding with one of the axle journals of the bearing;
an operating channel arranged between the axle journals in which a scalpel or another acting element is slidable between a proximal and a distal position; and
the basic body of the tool includes two parallel walls realized as webs on a base plate, between which a portion of the operating channel is arranged, each of the two parallel walls has a recess in which one of the two axle journals engages.

2. The tool of claim 1, wherein the bearing additionally includes recesses which correspond to the axle journals, and wherein the axle journals engage in the recesses from the outside.

3. The tool of claim 1, wherein the axle journal components are connected together in a rigid manner once the axle journals have been inserted into the corresponding recesses.

4. The tool of claim 3, wherein the axle journal components are connected together in a rigid manner by means of a basic body of the pivotable mouth part.

5. The tool of claim 1, further comprising:
a transferring device for transferring a force to the tool;
wherein the transferring device and the pivotable mouth part have curved sliding faces which abut against one another and are realized for the purpose of coupling a translation movement of the transferring device with a pivoting movement of the pivotable mouth part,
wherein a center of curvature of the curved sliding faces lies outside the tool.

6. The tool of claim 1, wherein a groove is provided inside a circular cylindrical region of space on at least one of the two axle journals, wherein the radial surfaces of the axle journals lie on a radial surface of the circular cylindrical region of space.

7. A medical instrument having a tool according to claim 1.

8. The tool of claim 1, wherein the two axle journals have a space between them, the space being a through-bore at a right angle with respect to the longitudinal axis and parallel with respect to the pivot axis.

9. A tool for a distal end or on a distal end of a shaft of a medical instrument, said tool comprising:
a basic body having a base plate extending substantially parallel with respect to a longitudinal axis of the shaft of the medical instrument, the basic body having a recess;
a mouth part which is pivotable about a pivot axis in relation to the basic body, the mouth part having a fixed mouth part and a pivotable mouth part;
a bearing arranged entirely in an interior of the tool, the bearing defining the pivot axis, the bearing including two axle journals, the two axle journals being spaced apart from one another along the pivot axis, each axle journal having a radial surface which is rotationally symmetrical with respect to the pivot axis, each axle journal being fit within the recess in the basic body;
the pivotable mouth part includes two axle journal components each corresponding with one of the axle journals of the bearing; and
an operating channel arranged between the axle journals in which an acting element is slidable between a proximal and a distal position.

10. The tool of claim 9, wherein the recess is a through-bore at right angles with respect to the longitudinal axis and parallel with respect to the pivot axis.

* * * * *